(12) United States Patent
Mitsuhashi et al.

(10) Patent No.: US 10,905,395 B2
(45) Date of Patent: Feb. 2, 2021

(54) DIAGNOSTIC IMAGING CATHETER

(71) Applicant: TERUMO KABUSHIKI KAISHA, Tokyo (JP)

(72) Inventors: Kenta Mitsuhashi, Shizuoka (JP); Yuuki Sakaguchi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 467 days.

(21) Appl. No.: 15/260,762

(22) Filed: Sep. 9, 2016

(65) Prior Publication Data

US 2017/0071568 A1 Mar. 16, 2017

(30) Foreign Application Priority Data

Sep. 10, 2015 (JP) ................................. 2015-178883

(51) Int. Cl.
*A61B 8/12* (2006.01)
*A61M 25/09* (2006.01)
(Continued)

(52) U.S. Cl.
CPC ................ *A61B 8/12* (2013.01); *A61B 8/445* (2013.01); *A61B 5/0066* (2013.01);
(Continued)

(58) Field of Classification Search
CPC ......... A61B 8/12; A61B 8/445; A61B 5/0066; A61B 5/6852; A61B 1/00068;
(Continued)

(56) References Cited

U.S. PATENT DOCUMENTS 5,024,234 A * 6/1991 Leary ................... A61B 8/12
600/467
5,445,155 A * 8/1995 Sieben ................. A61B 8/12
128/925
(Continued)

FOREIGN PATENT DOCUMENTS

JP  H06-125904 A   5/1994
JP  2000-189517 A  7/2000
(Continued)

OTHER PUBLICATIONS

Notice of Reasons for Refusal (Office Action) dated Feb. 25, 2019 in Japanese Patent Application No. 2015-178883.

*Primary Examiner* — Theodore J Stigell
*Assistant Examiner* — Amy J Shafqat
(74) *Attorney, Agent, or Firm* — Buchanan Ingersoll & Rooney PC

(57) ABSTRACT

A diagnostic imaging catheter is disclosed which includes a drive shaft, of which a distal portion is provided with a signal transmitting and receiving unit, and which can be rotated; a sheath including a lumen into which the drive shaft is inserted such that the drive shaft can be moved forward and backward; a communicating hole which is provided in a distal portion of the sheath, and through which the inside and the outside of the sheath communicate with each other; and a valve body capable of opening and closing the communicating hole. The valve body is configured to be capable of switching between a closed state in which the communicating hole is covered and blocked with the valve body and an open state which the valve body enters by being moved to the outside of the sheath from the closed state, and in which the communicating hole is open.

12 Claims, 9 Drawing Sheets

(51) Int. Cl.
*A61B 8/00* (2006.01)
*A61B 5/00* (2006.01)
*A61M 39/06* (2006.01)

(52) U.S. Cl.
CPC ............ *A61B 5/6852* (2013.01); *A61M 25/09* (2013.01); *A61M 2039/0646* (2013.01); *A61M 2039/0666* (2013.01)

(58) Field of Classification Search
CPC ........... A61B 5/0002; A61B 5/150221; A61M 39/00; A61M 2039/0673; A61M 25/00; A61M 5/00; A61M 25/09; A61M 2039/0666; A61M 1/0035; A61M 1/0043; A61M 1/0045; A61M 1/005; A61M 1/0052; A61M 1/1065; A61M 1/1075; A61M 1/1098; A61M 5/1408; A61M 5/16881; A61M 2005/3128; A61M 16/1015; A61M 16/164; A61M 16/167; A61M 16/209; A61M 16/207; A61M 25/0028; A61M 25/0029; A61M 25/003; A61M 2025/006; A61M 25/0067; A61M 25/0075; A61M 2025/0076; A61M 25/10185; A61M 25/10186; A61M 2039/027; A61M 2039/0036; A61M 39/06; A61M 2039/064; A61M 2039/0646; A61M 2039/0653; A61M 2039/066; A61M 39/26; A61M 39/22; A61M 39/223; A61M 2039/2433; A61M 2039/2473; A61M 2039/2493; A61M 2039/261; A61M 2039/262
See application file for complete search history.

(56) References Cited

U.S. PATENT DOCUMENTS

| | | | | |
|---|---|---|---|---|
| 5,545,142 | A * | 8/1996 | Stephens | A61B 17/3417 604/167.01 |
| 5,976,093 | A * | 11/1999 | Jang | A61B 8/12 600/462 |
| 6,475,187 | B1 | 11/2002 | Gerberding | |
| 8,740,849 | B1 * | 6/2014 | Fischell | A61M 25/0084 604/164.12 |
| 2006/0079740 | A1 * | 4/2006 | Silver | A61B 5/0031 600/309 |
| 2006/0241484 | A1 * | 10/2006 | Horiike | A61B 8/4416 600/467 |
| 2007/0232891 | A1 * | 10/2007 | Hirota | A61B 5/6852 600/407 |
| 2008/0146918 | A1 * | 6/2008 | Magnin | A61B 8/0841 600/437 |
| 2011/0077463 | A1 * | 3/2011 | Hirota | A61B 5/0066 600/114 |
| 2011/0178506 | A1 * | 7/2011 | Numata | A61M 25/002 604/528 |
| 2012/0004622 | A1 * | 1/2012 | Leeflang | A61M 39/06 604/246 |
| 2012/0136340 | A1 * | 5/2012 | Tanioka | A61M 25/0052 604/526 |
| 2012/0165680 | A1 * | 6/2012 | Akifumi | A61B 8/12 600/466 |
| 2014/0012209 | A1 * | 1/2014 | Sansoucy | A61M 25/003 604/247 |
| 2014/0163421 | A1 * | 6/2014 | Van Hoven | A61B 8/12 600/585 |
| 2014/0194704 | A1 * | 7/2014 | Millett | A61B 17/12113 600/301 |
| 2014/0221932 | A1 * | 8/2014 | Puhasmagi | A61M 25/0097 604/167.05 |
| 2014/0371598 | A1 * | 12/2014 | Okubo | A61B 8/12 600/467 |
| 2015/0005628 | A1 * | 1/2015 | Itoh | A61B 8/12 600/427 |
| 2016/0324503 | A1 * | 11/2016 | Norris | A61B 8/445 |
| 2017/0303891 | A1 * | 10/2017 | Yamashita | A61B 8/12 |
| 2018/0199916 | A1 * | 7/2018 | Sugihara | A61B 1/00154 |

FOREIGN PATENT DOCUMENTS

| | | |
|---|---|---|
| JP | 2002-505166 A | 2/2002 |
| JP | 2015-119994 A | 7/2015 |
| WO | WO 2008-086614 A1 | 7/2008 |
| WO | 2014/192146 A1 | 12/2014 |

* cited by examiner

DIAGNOSTIC IMAGING CATHETER

CROSS-REFERENCES TO RELATED APPLICATIONS

This application claims priority to Japanese Application No. 2015-178883 filed on Sep. 10, 2015, the entire content of which is incorporated herein by reference.

TECHNICAL FIELD

The present disclosure relates to a diagnostic imaging catheter.

BACKGROUND DISCUSSION

The related art discloses a diagnostic imaging catheter, which is used in imaging apparatuses for diagnosis such as an intravascular ultrasound (IVUS) and an optical coherence tomography (OCT), as a catheter used to acquire diagnostic images for diagnosing a disease site or the like inside a living body.

The diagnostic imaging catheter includes a drive shaft that is provided with a transmitting and receiving unit transmitting and receiving inspection waves, and a sheath including a lumen into which the drive shaft is inserted such that the drive shaft can be moved forward and backward. When the diagnostic imaging catheter is used, a so-called pull-back operation (inward pulling operation) is performed where the drive shaft is moved from a distal side toward a proximal side by moving the drive shaft backward, or a push operation is performed where the drive shaft is pushed toward the distal side (refer to JP-A-2015-119994).

When the diagnostic imaging catheter is used, the inside of the sheath is filled with priming liquid such as a physiological salt solution so as to efficiently transmit and receive inspection waves. Typically, a communicating hole is provided in a distal portion of the sheath so as to discharge the filled priming liquid to the outside of the sheath together with air inside the sheath, and the inside and the outside of the lumen communicate with each other via the communicating hole.

Since the communicating hole is open to the outside of the sheath, a user has to pay close attention to the use of the diagnostic imaging catheter such that air or blood is prevented from entering the inside of the sheath, and it takes some man hours to perform an operation. For example, if air enters the inside of the sheath, it is considered that ultrasonic waves are attenuated by the air and ultrasonic detection sensitivity of an ultrasound transducer decreases. If blood enters the inside of the sheath, it is considered that a diagnostic image becomes, for example, unsharp or not well defined, and the blood flows backward to a proximal side during a pull-back operation.

The present disclosure is made in light of these problems, and provides a diagnostic imaging catheter capable of releasing priming liquid inside a sheath during a priming process, and preventing the infiltration of air or blood into the sheath.

SUMMARY

A diagnostic imaging catheter is disclosed, which includes: a drive shaft, of which a distal portion is provided with a signal transmitting and receiving unit, and which can be rotated; a sheath including a lumen into which the drive shaft is inserted such that the drive shaft can be moved forward and backward; a communicating hole which is provided in a distal portion of the sheath, and through which the inside and the outside of the lumen communicate with each other; and a valve body capable of opening and closing the communicating hole. The valve body is configured to be capable of switching between a closed state in which the communicating hole is covered and blocked with the valve body and an open state which the valve body enters by being moved to the outside of the sheath from the closed state, and in which the communicating hole is open.

A diagnostic imaging catheter is disclosed comprising: a rotatable drive shaft, of which a distal portion is provided with a signal transmitting and receiving unit; a sheath including a lumen into which the drive shaft is inserted such that the drive shaft can be moved forward and backward; a communicating hole which is provided in a distal portion of the sheath, and through which an inside and an outside of the lumen communicate with each other; a valve body capable of opening and closing the communicating hole, wherein the valve body is configured to be capable of switching between a closed state in which the communicating hole is covered and blocked with the valve body and an open state which the valve body enters by being moved to the outside of the sheath from the closed state, and in which the communicating hole is open; a guide wire insertion member that is provided parallel to the lumen of the sheath, and includes a guide wire lumen into which a guide wire can be inserted, wherein the communicating hole communicates with the lumen and the guide wire lumen, the valve body is configured such that the valve body can be maintained in the closed state by pressing force received from the guide wire inserted into the guide wire lumen; and a restriction unit that restricts the valve body from entering the inside of the sheath by being attached to a tubular wall of the sheath when the valve body is in the closed state.

In the diagnostic imaging catheter having the aforementioned configuration, if the valve body is brought into an open state in which the communicating hole is open, priming liquid can be released from the inside of the sheath to the outside. In contrast, if the valve body is brought into a closed state in which the communicating hole is covered and blocked with the valve body, the infiltration of air or blood into the sheath can be prevented from the outside of the sheath.

BRIEF DESCRIPTION OF THE DRAWINGS

FIGS. 2A and 2B show schematic views illustrating the entire configuration of the diagnostic imaging catheter of the embodiment of the present invention, wherein FIG. 2A is a side view of the diagnostic imaging catheter before a pull-back operation (inward pulling operation) is performed; and FIG. 2B is a side view of the diagnostic imaging catheter when the pull-back operation is performed.

FIGS. 3A-3D show views illustrating the configuration of a distal side of the diagnostic imaging catheter of a first embodiment, wherein FIG. 3A illustrates a state in which a valve body is open; FIG. 3B illustrates a state in which the valve body is closed; FIG. 3C is an enlarged view of the valve body; and FIG. 3D is a sectional view taken along line 3D-3D in FIG. 3C.

FIGS. 5A-5D show views illustrating the configuration of a distal side of a diagnostic imaging catheter of Modification Example 1, wherein FIG. 5A illustrates a state in which a valve body is open; FIG. 5B illustrates a state in which the valve body is closed; FIG. 5C is an enlarged view of the valve body; and FIG. 5D is a sectional view taken along line 5D-5D in FIG. 5C.

FIGS. 6A-6D show views illustrating the configuration of a distal side of a diagnostic imaging catheter of Modification Example 2, wherein FIG. 6A illustrates a state in which a valve body is open; FIG. 6B illustrates a state in which the valve body is closed; FIG. 6C is an enlarged perspective view illustrating a state in which the valve body is open; and FIG. 6D is an enlarged perspective view illustrating a state in which the valve body is closed.

FIGS. 9A-9B show views illustrating the configuration of a distal side of the diagnostic imaging catheter of the second embodiment, wherein FIG. 9A illustrates a state in which a valve body is open; and FIG. 9B illustrates a state in which the valve body is closed.

DETAILED DESCRIPTION

Figure 1:
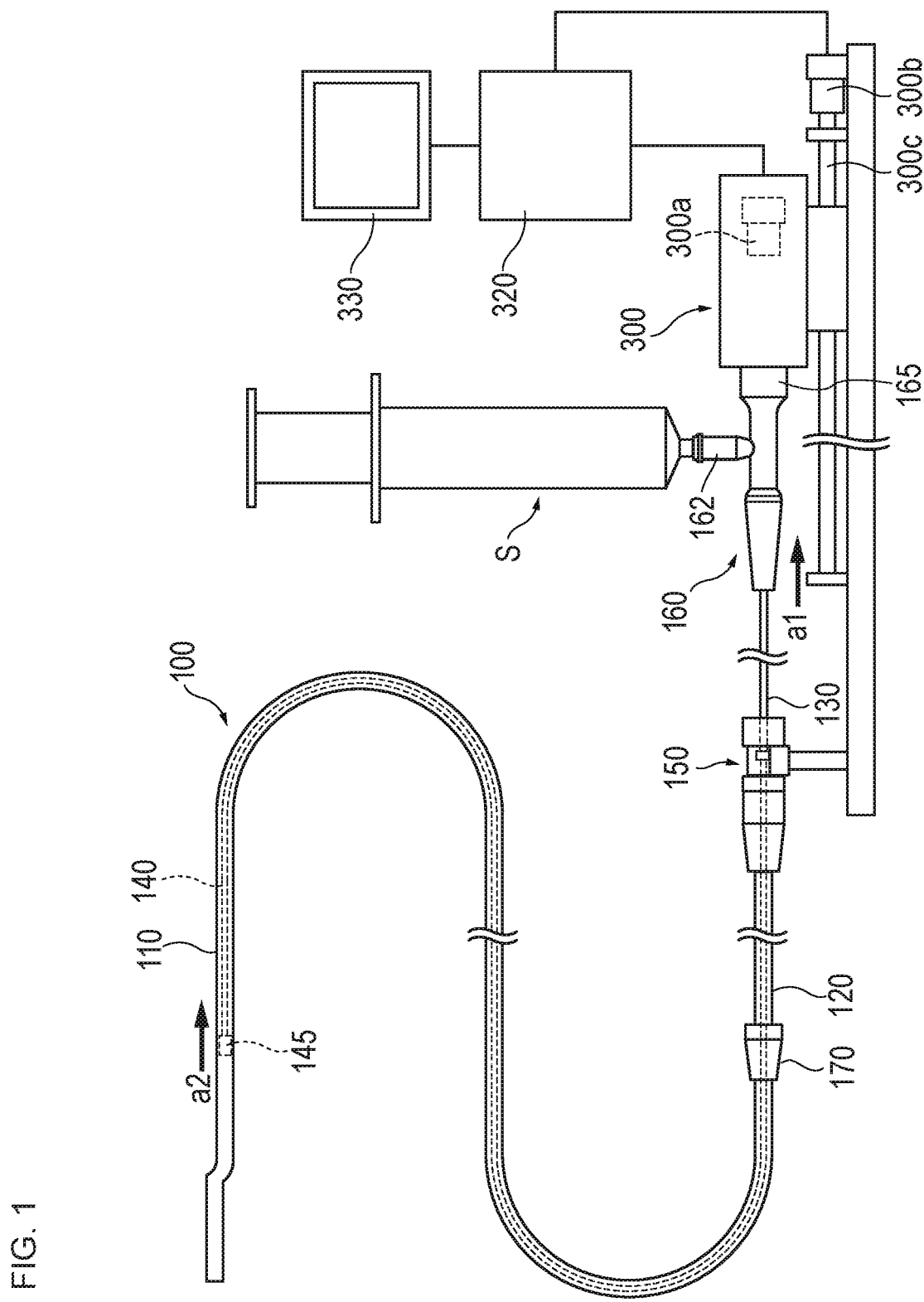
FIG. 1 is a plan view illustrating a state in which an external apparatus is connected to a diagnostic imaging catheter of an embodiment of the present invention.

Hereinafter, embodiments of the present invention will be described with reference to the accompanying drawings. The following description does not set limits to the technical concept described in the claims or the meanings of terms. For illustrative purposes, dimensional ratios in the drawings may be exaggerated, and may be different from actual ratios.

Figure 2A:
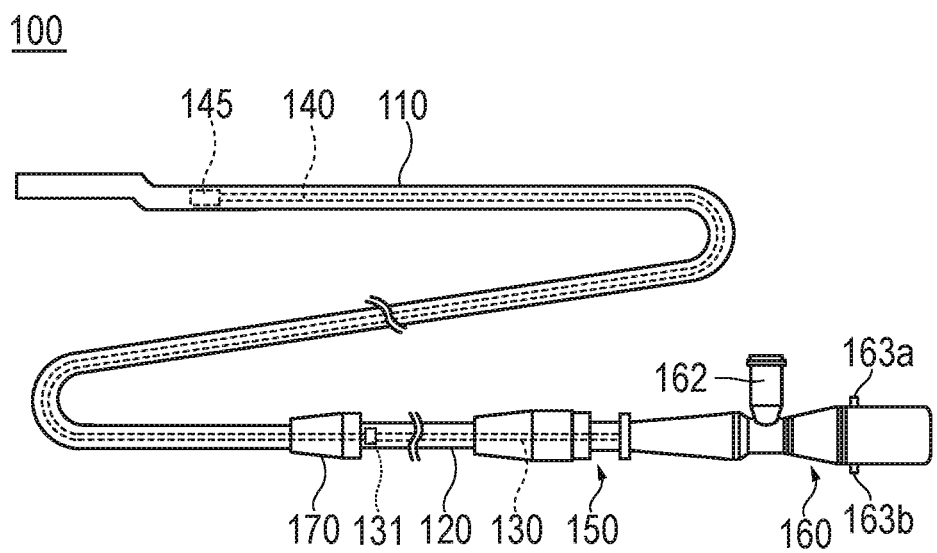
Figure 2B:
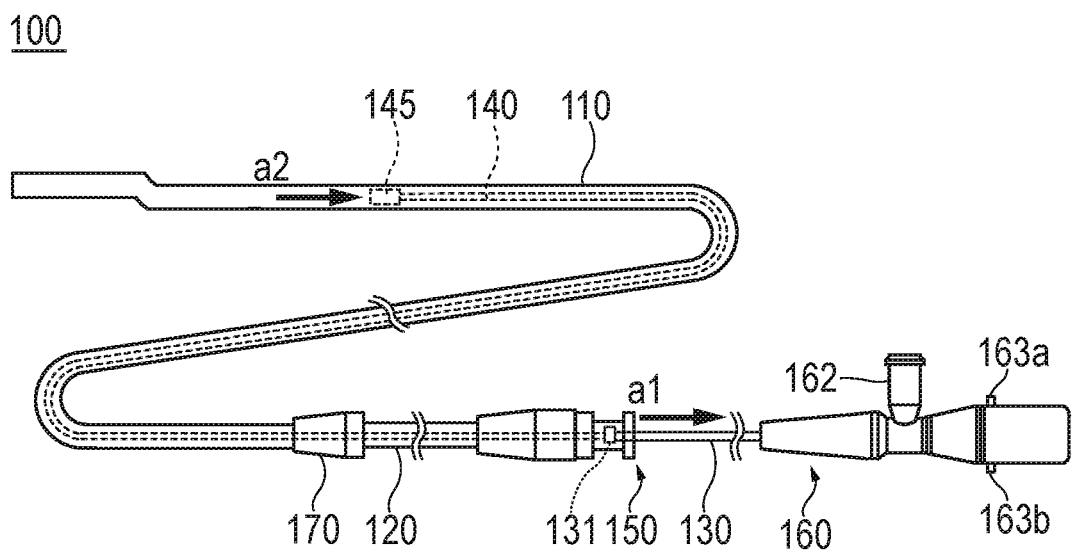
Figure 3A:
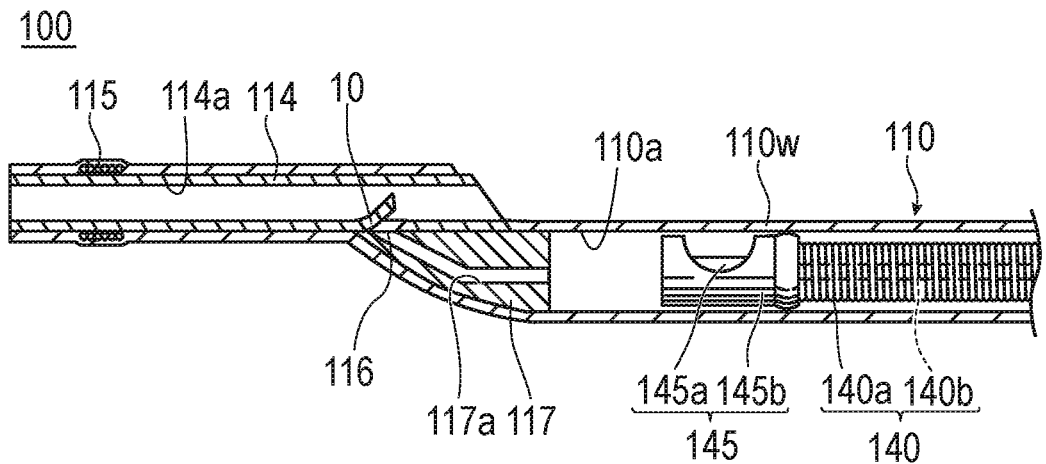

FIG. 1 is a plan view illustrating a state in which an external apparatus 300 is connected to a diagnostic imaging catheter 100 of a first embodiment. FIGS. 2A and 2B show views illustrating the entire configuration of the diagnostic imaging catheter 100 of the first embodiment. FIGS. 3A-3D show views illustrating the configuration of a distal side of the diagnostic imaging catheter of the first embodiment. FIG. 4 is a view illustrating the configuration of a proximal side (hand-side) of the diagnostic imaging catheter of the first embodiment.

The diagnostic imaging catheter 100 of the embodiment is an intravascular ultrasound (IVUS). As illustrated in FIG. 1, the diagnostic imaging catheter 100 is connected to and is driven by the external apparatus 300.

The diagnostic imaging catheter 100 will be described with reference to FIGS. 1 to 4.

As illustrated in FIGS. 1, 2A and 2B, briefly, the diagnostic imaging catheter 100 can include a sheath 110 that is inserted into a body-cavity of a living body; an outer tube 120 that is provided on a proximal side of the sheath 110; an inner shaft 130 which is inserted into the outer tube 120 such that the inner shaft 130 can be moved forward and backward inside of the outer tube 120; a drive shaft 140 that includes a signal transmitting and receiving unit 145, which transmits and receives signals, at a distal end of the drive shaft 140, and is rotatably provided inside the sheath 110; a unit connector 150 which is configured such that the unit connector 150 is provided on a proximal side of the outer tube 120 and accommodates the inner shaft 130; and a hub 160 that is provided on a proximal side of the inner shaft 130. As illustrated in FIG. 3A, the diagnostic imaging catheter 100 further can include a guide wire insertion member 114 including a guide wire lumen 114a into which a guide wire W can be inserted; a communicating hole 116 through which the inside and the outside of a lumen 110a communicate with each other; a valve body 10 capable of opening and closing the communicating hole 116; and a restriction unit 20 (refer to FIG. 3D) that restricts the valve body 10 from entering the inside of the sheath 110.

In the description of the specification, a distal end or a distal side refers to a side of the diagnostic imaging catheter 100 which is inserted into a body-cavity. A proximal end or a proximal side refers to a side of the diagnostic imaging catheter 100 on which the hub 160 is provided. An axial direction refers to an extending direction of the sheath 110.

As illustrated in FIG. 2A, the drive shaft 140 extends up to the inside of the hub 160 through the sheath 110, the outer tube 120 connected to a proximal end of the sheath 110, and the inner shaft 130 inserted into the outer tube 120.

The hub 160, the inner shaft 130, the drive shaft 140, and the signal transmitting and receiving unit 145 are connected to each other such that the hub 160, the inner shaft 130, the drive shaft 140, and the signal transmitting and receiving unit 145 can be integrally moved forward and backward in the axial direction. For this reason, for example, if the hub 160 is pushed toward the distal side, the inner shaft 130 connected to the hub 160 is pushed into the outer tube 120 and the unit connector 150, and the drive shaft 140 and the signal transmitting and receiving unit 145 are moved inside the sheath 110 toward the distal side. For example, if the hub 160 is pulled toward the proximal side, as illustrated by an arrow a1 in FIGS. 1 and 2B, the inner shaft 130 is pulled out from the outer tube 120 and the unit connector 150, and as illustrated by an arrow a2, the drive shaft 140 and the signal transmitting and receiving unit 145 are moved inside the sheath 110 toward the proximal side.

As illustrated in FIG. 2A, if the inner shaft 130 is pushed the maximum distance toward the distal side, a distal portion of the inner shaft 130 reaches the vicinity of a relay connector 170. At this time, the signal transmitting and receiving unit 145 is positioned in the vicinity of the distal end of the sheath 110. The relay connector 170 is a connector through which the sheath 110 is connected to the outer tube 120.

As illustrated in FIG. 2B, a falling-out preventive connector 131 is provided at a distal end of the inner shaft 130. The falling-out preventive connector 131 has the function of preventing the falling out of the inner shaft 130 from the outer tube 120. The falling-out preventive connector 131 is configured such that if the hub 160 is pulled the maximum distance toward the proximal side, that is, for example, if the inner shaft 130 is pulled the maximum distance out from the outer tube 120 and the unit connector 150, the falling-out preventive connector 131 is hooked to an inner wall of the unit connector 150 at a predetermined position.

As illustrated in FIG. 3A, the drive shaft 140 can include a flexible pipe body 140a, and a signal cable 140b inserted into the pipe body 140a. The pipe body 140a may be configured of multiple layers of coils having different winding directions around the axis. Examples of the material of the coil can include, for example, stainless steel and a nickel-titanium (Ni—Ti) alloy. The signal cable 140b may be configured of a twisted pair cable or a coaxial cable.

The signal transmitting and receiving unit 145 can include an ultrasound transducer 145a that transmits and receives ultrasonic waves, and a housing 145b that accommodates the ultrasound transducer 145a.

The ultrasound transducer 145a has the function of transmitting ultrasonic waves, which are inspection waves, into a body-cavity, and receiving ultrasonic waves reflected from the body-cavity. The ultrasound transducer 145*a* is electrically connected to an electrode terminal 166 (refer to FIG. 4) via the signal cable 140*b*.

The ultrasound transducer 145*a* may be made of a piezoelectric material such as ceramic or a crystal.

As illustrated in FIG. 3A, the sheath 110 can include the lumen 110*a* into which the drive shaft 140 is inserted such that the drive shaft 140 can be moved forward and backward. The guide wire insertion member 114, which can include the guide wire lumen 114*a* into which the guide wire W can be inserted, is attached to a distal portion of the sheath 110 in such a way that the guide wire insertion member 114 is provided parallel to the lumen 110*a* provided in the sheath 110.

The communicating hole 116, through which the inside of the lumen 110*a* communicates with the guide wire lumen 114*a* disposed outside the lumen 110*a*, is formed in a side surface of the sheath 110 to which the guide wire insertion member 114 is attached.

A reinforcement member 117 is provided in the distal portion of the sheath 110, and can be rigidly joined to and supports the guide wire insertion member 114. The reinforcement member 117 is provided with a communicating passage 117*a* through which the communicating hole 116 communicates with the inside of the lumen 110*a* which is disposed closer to the proximal side than the reinforcement member 117.

In accordance with an exemplary embodiment, the communicating hole 116 is a priming liquid discharge hole through which the priming liquid is discharged. When the diagnostic imaging catheter 100 is used, a priming process is performed in which the inside of the sheath 110 is filled with the priming liquid so as to reduce the attenuation of ultrasonic waves caused by air inside the sheath 110 and to efficiently transmit and receive ultrasonic waves. In accordance with an exemplary embodiment, a gas such as air can be discharged from the inside of the sheath 110 together with the priming liquid by releasing the priming liquid through the communicating hole 116.

Figure 3B:
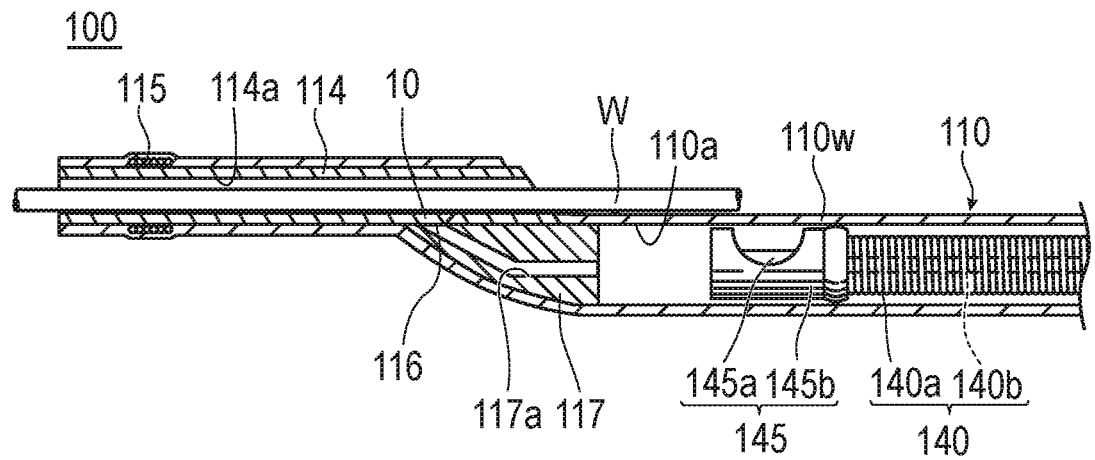
Figure 4:
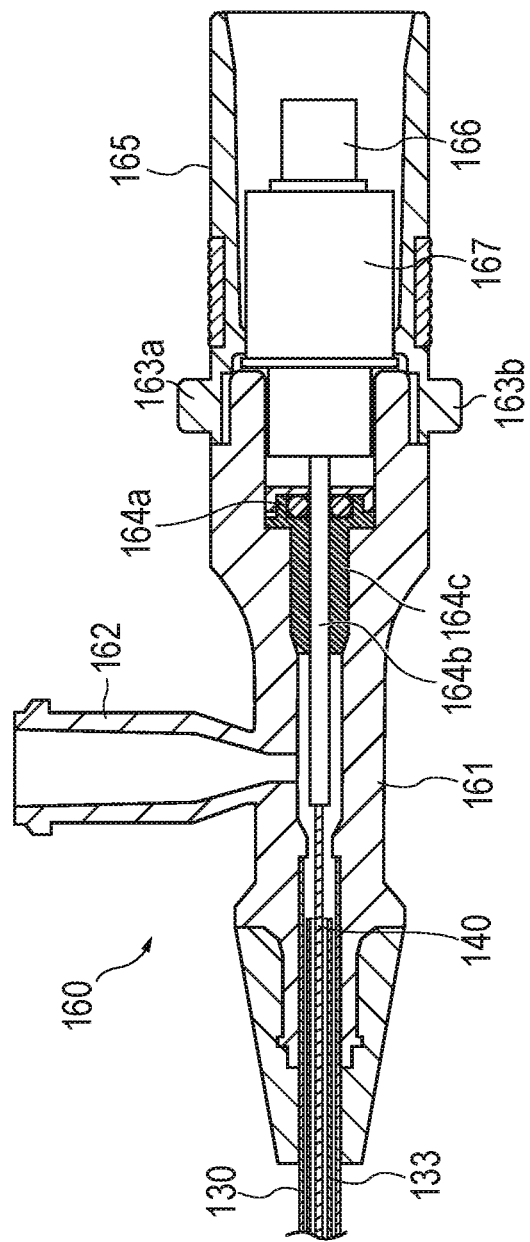
FIG. 4 is a view illustrating the configuration of a proximal side (hand-side) of the diagnostic imaging catheter of the first embodiment.

The valve body 10 is configured to be capable of switching between an "open state" in which the communicating hole 116 is open as illustrated in FIG. 3A and a "closed state" in which the communicating hole 116 is covered and blocked with the valve body 10 as illustrated in FIG. 3B. Specifically, for example, if the priming liquid is injected into the sheath 110 in the priming process, pressure is applied to the inside of the lumen 110*a*. The valve body 10 is pressed toward the outside of the sheath 110 by the pressure. As illustrated in FIG. 3A, the valve body 10 is configured such that the valve body 10 can be moved toward the outside of the sheath 110, and can be maintained in an open state in which the communicating hole 116 is open. If the guide wire W is inserted into the guide wire lumen 114*a*, the valve body 10 receives pressing force from the guide wire W. As illustrated in FIG. 3B, the valve body 10 is configured such that the valve body 10 can be maintained in a closed state. Hereinafter, the configuration of the valve body 10 will be described in detail.

Figure 3C:
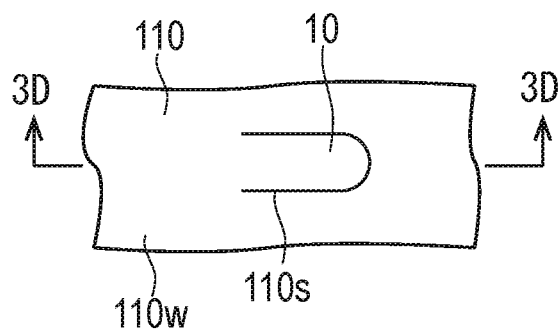
Figure 3D:
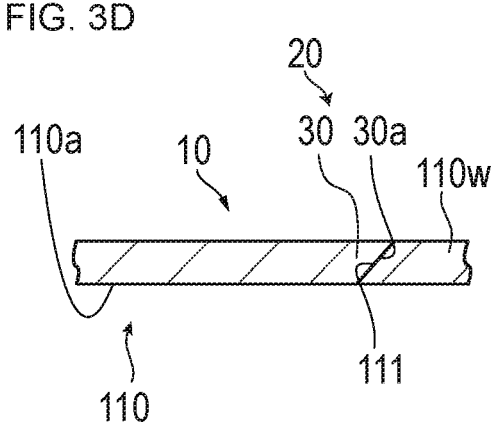

As illustrated in FIGS. 3C and 3D, the valve body 10 is configured of a portion of a tubular wall 110*w* of the sheath 110. The valve body 10 is formed by providing a slit 110*s* in the portion of the tubular wall 110*w* which passes therethrough up to the inside of the lumen 110*a*. As illustrated in FIG. 3C, the slit 110*s* can be formed into a U shape. The valve body 10 is configured such that the portion, in which the slit 110*s* is provided, is deformed to curl up toward the distal side and the valve body 10 enters an open state.

As illustrated in FIG. 3D, a proximal portion of the valve body 10 can include a cutout portion 30 including an inclined surface 30*a* that is formed by providing the slit 110*s* obliquely relative to a thickness direction of the tubular wall 110*w*. The tubular wall 110*w* can include an inclined surface 111 facing the inclined surface 30*a* of the cutout portion 30.

In accordance with an exemplary embodiment, the valve body 10 is configured such that when the valve body 10 is in a closed state, the inclined surface 30*a* of the cutout portion 30 is attached to the inclined surface 111 of the tubular wall 110*w* of the sheath 110. Since the inclined surface 30*a* is attached to the inclined surface 111, the valve body 10 is restricted from entering the inside of the lumen 110*a*. As such, in the embodiment, the restriction unit 20 is configured of the cutout portion 30.

The sheath 110 is formed of a material having a high ultrasonic transmissivity. The distal portion of the sheath 110, which is disposed in a range of area where the ultrasound transducer 145*a* is moved in the axial direction of the sheath 110, configures an acoustic window portion having ultrasonic transmissivity higher than those of other portions.

The sheath 110, the guide wire insertion member 114, and the reinforcement member 117 can be integrally formed via heat-welding.

The sheath 110, the guide wire insertion member 114, and the reinforcement member 117 are formed of a flexible material, and the material thereof is not limited to a specific material. Examples of the flexible material for the sheath 110, the guide wire insertion member 114, and the reinforcement member 117 can include various thermoplastic elastomers such as a styrene elastomer, a polyolefin elastomer, a polyurethane elastomer, a polyester elastomer, a polyamide elastomer, a polyimide elastomer, a polybutadiene elastomer, a trans-polyisoprene elastomer, a fluororubber elastomer, and a chlorinated polyethylene elastomer. A combination of one or two or more (polymer alloy, polymer blend, or laminated body) of these may be also used as the material. A hydrophilic lubricant coating layer which shows lubricating ability when is wet may be disposed on an exterior surface of the sheath 110.

The guide wire insertion member 114 is provided with a marker 115 having high X-ray contrast properties. The marker 115 is configured of a metal coil made of Pt, Au, or Ir, having high radiopaque properties.

As illustrated in FIG. 4, the hub 160 can include a hub main body 161 having a hollow shape; a port 162 that communicates with the inside of the hub main body 161; orientation confirmation projections 163*a* and 163*b* used to confirm the orientation of the hub 160 when connecting the hub 160 to the external apparatus 300; a seal member 164*a* that seals a portion of the hub 160 which is closer to the proximal side than the port 162; a connection pipe 164*b* that holds the drive shaft 140; a bearing 164*c* that rotatably supports the connection pipe 164*b*; and a connector unit 165 inside which the electrode terminal 166, which is mechanically and electrically connected to the external apparatus 300, is disposed.

The inner shaft 130 is connected to a distal portion of the hub main body 161. The drive shaft 140 is pulled out from the inner shaft 130 inside the hub main body 161. A protective tube 133 is disposed between the inner shaft 130 and the drive shaft 140. The protective tube 133 has the function of preventing the occurrence of damage to the drive shaft 140 caused by interference between the inner shaft 130 and the drive shaft 140.

The connection pipe 164b holds the drive shaft 140 via a distal end of the connection pipe 164b which is an end portion of the connection pipe 164b opposite to a rotor 167, so as to transmit rotation of the rotor 167 to the drive shaft 140. The signal cable 140b (refer to FIG. 3A) is inserted into the connection pipe 164b. One end of the signal cable 140b is connected to the electrode terminal 166, and the other end of the signal cable 140b is connected to the ultrasound transducer 145a through the inside of the drive shaft 140. A received signal of the ultrasound transducer 145a is transmitted to the external apparatus 300 via the electrode terminal 166, is subjected to a predetermined process, and is displayed as an image.

With reference to FIG. 1 again, the diagnostic imaging catheter 100 is connected to and is driven by the external apparatus 300.

As described above, the external apparatus 300 is connected to the connector unit 165 provided on a proximal side of the hub 160.

The external apparatus 300 can include a motor 300a which is a power source rotating the drive shaft 140, and a motor 300b which is a power source moving the drive shaft 140 in the axial direction. A ball screw 300c connected to the motor 300b can convert a rotational motion of the motor 300b into an axial motion.

The operation of the external apparatus 300 is controlled by a control apparatus 320 that is electrically connected to the external apparatus 300. The control apparatus 320 can include a central processing unit (CPU) and a memory as main configuration elements. The control apparatus 320 is electrically connected to a monitor 330.

Hereinafter, an example of usage of the diagnostic imaging catheter 100 will be described.

First, as illustrated in FIG. 1, a user connects the external apparatus 300 to the connector unit 165 of the diagnostic imaging catheter 100. Thereafter, the user connects a syringe S, which is filled with priming liquid, to the port 162, and injects the priming liquid into the lumen 110a of the sheath 110 by pressing a plunger of the syringe S.

As illustrated in FIG. 3A, if the priming liquid is injected into the lumen 110a, the internal pressure of the lumen 110a is increased by the pressure of the priming liquid, and the valve body 10 is pressed, such that the valve body 10 can be moved toward the outside of the sheath 110, and enters an open state in which the communicating hole 116 is open. As a result, a gas such as air can be discharged from the inside of the sheath 110 together with the priming liquid by releasing the priming liquid through the communicating hole 116.

After the priming process, as illustrated in FIG. 2A, the user moves the signal transmitting and receiving unit 145 toward the distal side by pressing the hub 160 until the hub 160 is attached to a proximal end of the unit connector 150. In this state, the user inserts the sheath 110 to a target position inside a body-cavity (for example, blood vessel) along the guide wire W while inserting the guide wire W into the guide wire lumen 114a. If the guide wire W is inserted into the guide wire lumen 114a, the valve body 10 receives pressure from the guide wire W. As illustrated in FIG. 3B, the valve body 10 is maintained in a closed state by the pressing force.

As illustrated in FIG. 3B, if the valve body 10 is in a closed state, the valve body 10 is accommodated in the communicating hole 116. As a result, it is possible to smoothly insert the guide wire W without the valve body 10 obstructing insertion of the guide wire W.

In order to obtain a tomographic image of the target position inside the body-cavity, as illustrated in FIG. 2B, the signal transmitting and receiving unit 145 transmits and receives ultrasonic waves while being moved toward the proximal side together with the drive shaft 140. The signal transmitting and receiving unit 145 is rotated together with the drive shaft 140.

If the drive shaft 140 is moved from the distal side toward the proximal side, the internal pressure of the communicating hole 116 decreases. Accordingly, the valve body 10 is pulled toward the inside of the sheath 110. Since the inclined surface 30a of the cutout portion 30 is attached to the inclined surface 111 of the tubular wall 110w, the valve body 10 can be restricted from entering the inside of the sheath 110.

The control apparatus 320 controls the rotation of the drive shaft 140 around the axis by controlling the motor 300a illustrated in FIG. 1. The control apparatus 320 controls the axial movement of the drive shaft 140 by controlling the motor 300b.

The signal transmitting and receiving unit 145 transmits ultrasonic waves into a body based on a signal transmitted from the control apparatus 320. A signal corresponding to reflected waves received by the signal transmitting and receiving unit 145 is transmitted to the control apparatus 320 via the drive shaft 140 and the external apparatus 300. The control apparatus 320 generates a tomographic image of the body-cavity based on the signal transmitted from the signal transmitting and receiving unit 145, and displays the generated image on the monitor 330.

The connector unit 165 provided inside the hub 160 is rotated while being connected to the external apparatus 300, and the drive shaft 140 is rotated in conjunction with the rotation. For example, the rotational speed of the connector unit 165 and the drive shaft 140 is 1800 rpm.

As described above, the diagnostic imaging catheter 100 of the embodiment can include the rotatable drive shaft 140, of which the distal portion is provided with the signal transmitting and receiving unit 145; the sheath 110 including the lumen 110a into which the drive shaft 140 is inserted such that the drive shaft 140 can be moved forward and backward; the communicating hole 116 which is provided in the distal portion of the sheath 110, and through which the inside and the outside of the lumen 110a communicate with each other; and the valve body 10 capable of opening and closing the communicating hole 116. The valve body 10 is configured to be capable of switching between a closed state in which the communicating hole 116 is covered and blocked with the valve body 10 and an open state which the valve body 10 enters by being moved to the outside of the sheath 110 from the closed state, and in which the communicating hole 116 is open.

In the diagnostic imaging catheter 100 having such a configuration, if the valve body 10 is brought into an open state in which the communicating hole 116 is open, priming liquid can be released from the inside of the lumen 110a to the outside. In contrast, if the valve body 10 is brought into a closed state in which the communicating hole 116 is covered and blocked with the valve body 10, the infiltration of air or blood into the sheath 110 can be prevented from the outside of the sheath 110. The diagnostic imaging catheter 100 further includes the restriction unit 20 that restricts the valve body 10 from entering the inside of the sheath 110 by being attached to the tubular wall 110w of the sheath 110 when the valve body 10 is in a closed state. Accordingly, the occurrence of a gap between the valve body 10 and the tubular wall 110w can be prevented. As a result, the infiltration of air or blood into the sheath 110 can be prevented.

The restriction unit 20 is configured of the cutout portion 30 that is formed by cutting out a portion of the tubular wall 110w of the sheath 110. The valve body 10 in a closed state is attached to the cutout portion 30. Since the restriction unit 20 is configured of a portion of the tubular wall 110w of the sheath 110, it is not necessary to add a separate member. As a result, it is possible to prevent an increase in manufacturing costs.

The communicating hole 116 communicates with the lumen 110a and the guide wire lumen 114a. The valve body 10 is configured such that the valve body 10 can be maintained in a closed state by pressing force received from the guide wire W inserted into the guide wire lumen 114a. If the sheath 110 is inserted into a body-cavity, the valve body 10 can be maintained in a closed state via the guide wire W inserted into the guide wire lumen 114a. As a result, it is possible to improve the efficiency of an operation by reducing man hours required to maintain the valve body 10 in a closed state.

FIGS. 5A-5D show views illustrating the configuration of a distal side of a diagnostic imaging catheter 100a of Modification Example 1.

Hereinafter, a valve body 11 of Modification Example 1 will be described with reference to FIGS. 5A-5D. The same reference signs are assigned to the same configuration elements as those in the first embodiment, and description thereof is omitted.

A restriction unit 21 of the diagnostic imaging catheter 100a of Modification Example 1 has a configuration different from that of the restriction unit 20 of the diagnostic imaging catheter 100 of the first embodiment.

Figure 5A:
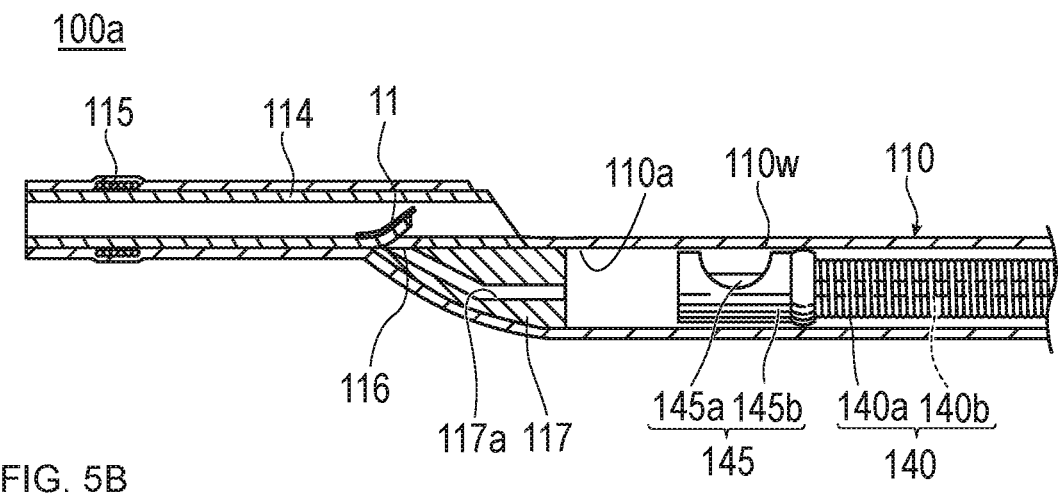
Figure 5B:
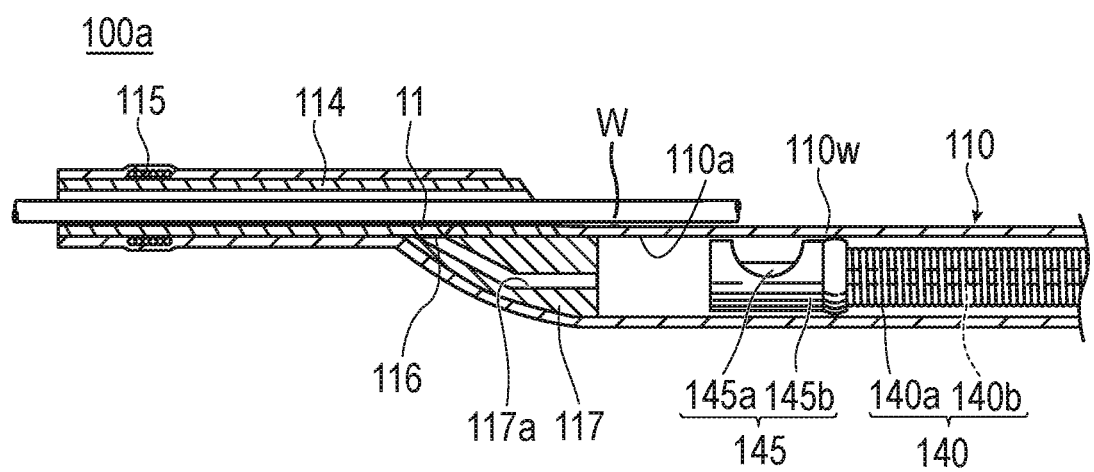

Similar to the first embodiment, the valve body 11 of Modification Example 1 is configured to be capable of switching between an "open state" in which the communicating hole 116 is open as illustrated in FIG. 5A and a "closed state" in which the communicating hole 116 is covered and blocked with the valve body 11 as illustrated in FIG. 5B. As illustrated in FIG. 5B, the valve body 11 is configured such that the valve body 11 can be maintained in a closed state by pressing force received from the guide wire W inserted into the guide wire lumen 114a.

Figure 5C:
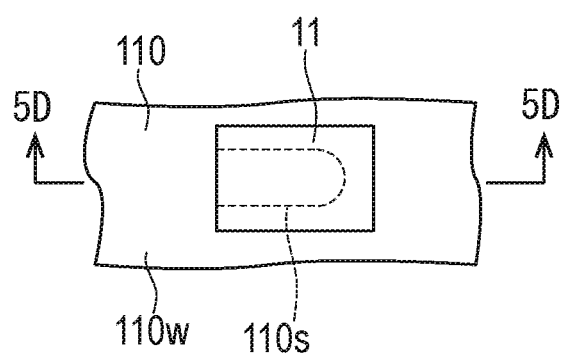
Figure 5D:
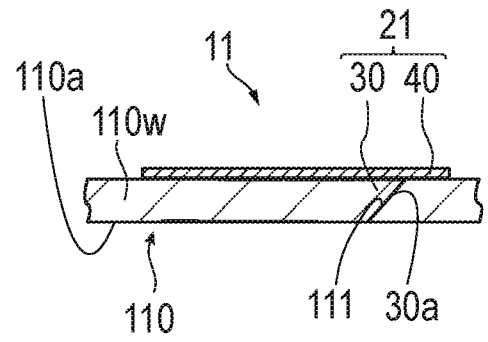

As illustrated in FIGS. 5C and 5D, the valve body 11 is formed by providing the slit 110s in a portion of the tubular wall 110w of the sheath 110, and is configured of the portion of the tubular wall 110w. A distal portion of the valve body 11 is provided with the cutout portion 30 that is formed by cutting out a portion of the tubular wall 110w of the sheath 110.

The restriction unit 21 of Modification Example 1 can include the cutout portion 30 and an attachment portion 40.

The attachment portion 40 is configured of a plate-shaped member. As illustrated in FIG. 5D, the attachment portion 40 is provided on an exterior surface of the valve body 11, and can be fixed to the valve body 11 via welding or adhesion. The attachment portion 40 can include a portion extending further from the valve body 11 toward the proximal side. The valve body 11 is configured such that when the valve body 11 is in a closed state, the extending portion of the attachment portion 40 is attached to an exterior surface of the tubular wall 110w which is positioned on a proximal side of the valve body 11.

The attachment portion 40 is formed of a flexible material and the same materials as those of the sheath 110 may be used.

In the diagnostic imaging catheter 100a of Modification Example 1 having such a configuration, it is possible to more reliably prevent the occurrence of a gap between the valve body 11 and the tubular wall 110w in comparison with that in a case where the restriction unit 20 is configured of only the cutout portion 30 as in the first embodiment. As a result, the infiltration of air or blood into the sheath 110 can be further prevented.

FIGS. 6A-6D show views illustrating the configuration of a distal side of a diagnostic imaging catheter 100b of Modification Example 2.

Hereinafter, a valve body 12 of Modification Example 2 will be described with reference to FIGS. 6A-6D. The same reference signs are assigned to the same configuration elements as those in the first embodiment, and description thereof is omitted.

The valve body 12 of the diagnostic imaging catheter 100b of Modification Example 2 has a configuration different from that of the diagnostic imaging catheter 100 of the first embodiment.

Figure 6A:
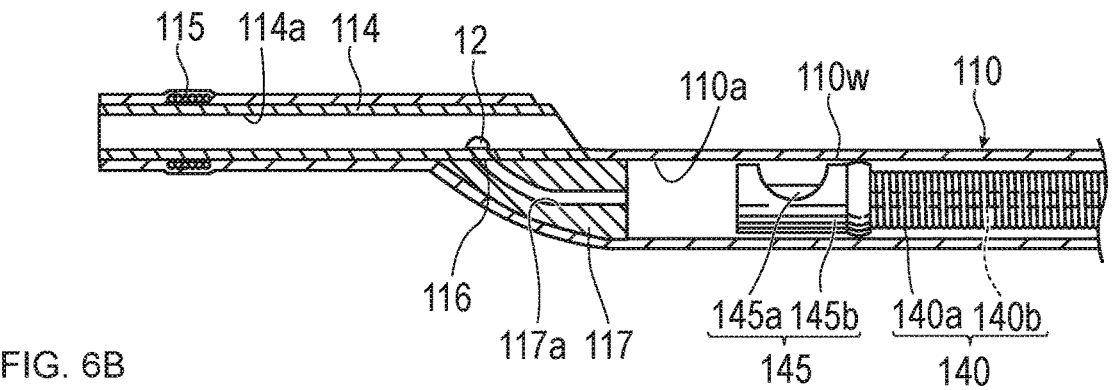
Figure 6B:
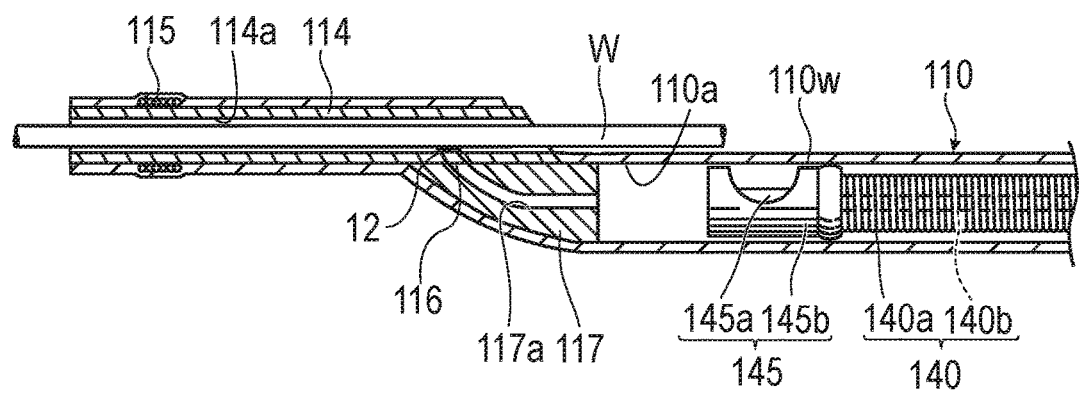

Similar to the first embodiment, the valve body 12 of Modification Example 2 is configured to be capable of switching between an "open state" in which the communicating hole 116 is open as illustrated in FIG. 6A and a "closed state" in which the communicating hole 116 is covered and blocked with the valve body 12 as illustrated in FIG. 6B. As illustrated in FIG. 6B, the valve body 12 is configured such that the valve body 12 can be maintained in a closed state by pressing force received from the guide wire W inserted into the guide wire lumen 114a.

Figure 6C:
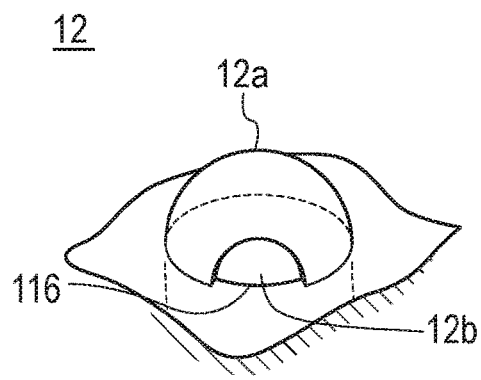

As illustrated in FIG. 6C, the valve body 12 of Modification Example 2 can include a body portion 12a that covers the periphery of the communicating hole 116, and an opening portion 12b which is formed in the body portion 12a and through which the outside of the sheath 110 communicates with the communicating hole 116.

The body portion 12a divides a space, which covers the periphery of the communicating hole 116 and communicates with the communicating hole 116, from the outside of the sheath 110. The body portion 12a is configured of a hollow elastic member having a hemispherical shape. The body portion 12a is configured such that the body portion 12a can be deformed by pressing force received from the guide wire W which will be described later. As illustrated in FIG. 6C, before the body portion 12a is deformed, the opening portion 12b is maintained in an open state in which the outside of the sheath 110 communicates with the communicating hole 116.

Figure 6D:
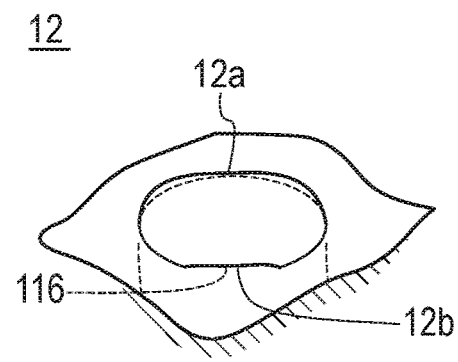

As illustrated in FIG. 6B, if the guide wire W is inserted into the guide wire lumen 114a, the body portion 12a is deformed by pressing force received from the guide wire W. As illustrated in FIG. 6D, the opening portion 12b is blocked by deformation of the body portion 12a. As such, due to the pressing force received from the guide wire W, the valve body 12 is maintained in a closed state in which the communicating hole 116 is covered and blocked with the valve body 12. Since the body portion 12a is formed into a hemispherical shape, it is possible to reduce contact resistance when inserting the guide wire W, and to smoothly insert the guide wire W. The shape of the valve body 12 is not limited to a hemispherical shell shape, and may be, for example, a rectangular parallelepiped shape or a triangular pyramid shape.

The valve body 12 can be fixed to the tubular wall 110w of the sheath 110 via welding or adhesion.

Insofar as an elastic member is used as the material of the valve body 12, the elastic member is not limited to a specific type of elastic member. Examples of the material include silicone rubber, latex rubber, butyl rubber, and isoprene rubber. The valve body 12 may be formed integrally with the sheath 110.

In the diagnostic imaging catheter 100b of Modification Example 2 having such a configuration, if the valve body 12 is brought into an open state in which the communicating hole 116 is open, priming liquid can be released from the inside of the lumen 110a to the outside. In contrast, if the valve body 12 is brought into a closed state in which the communicating hole 116 is covered and blocked with the valve body 12, the infiltration of air or blood into the lumen 110a from the outside of the lumen 110a can be prevented.

Figure 7:
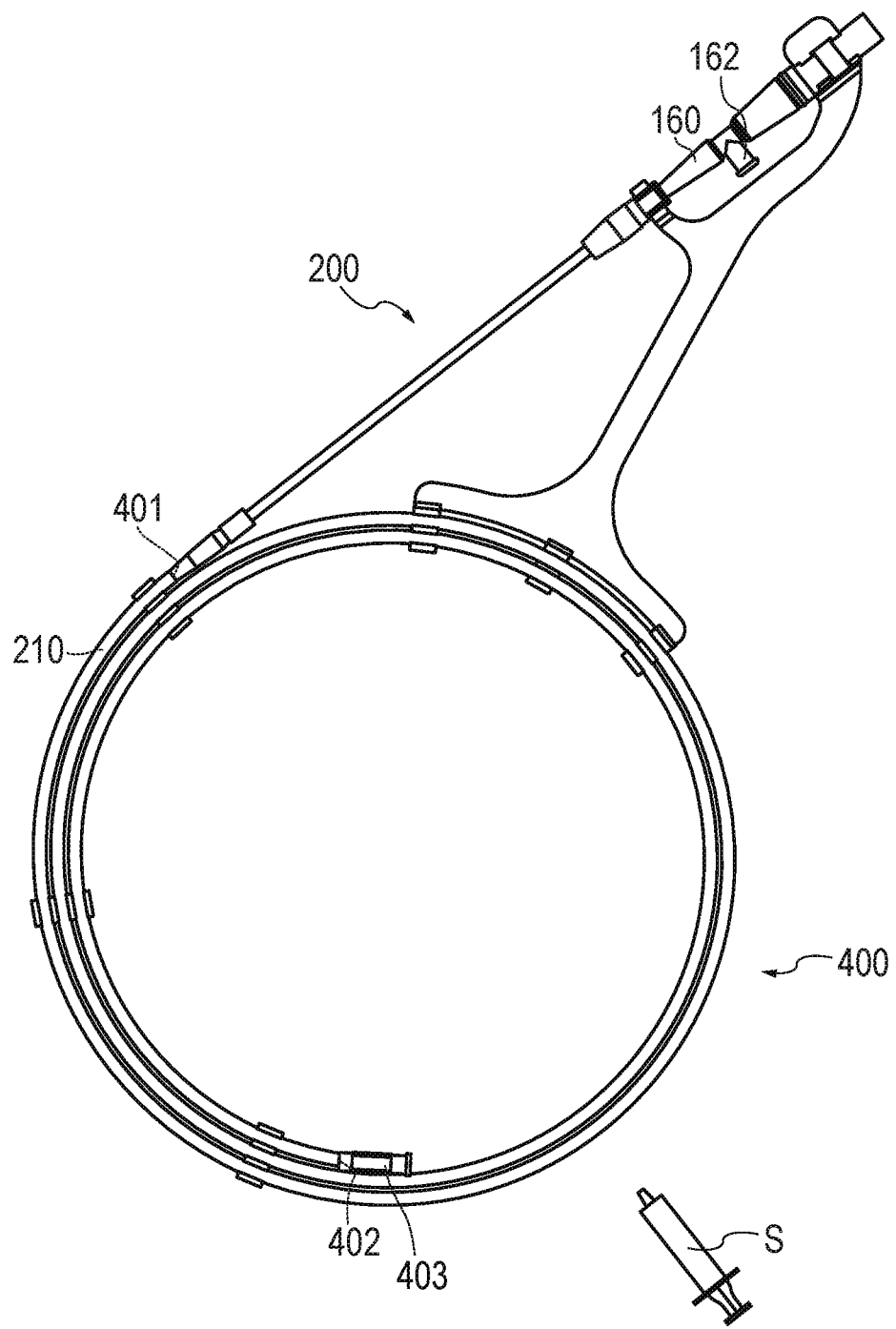
FIG. 7 is a side view illustrating a state in which a diagnostic imaging catheter of a second embodiment is accommodated inside a holder tube.
Figure 8:
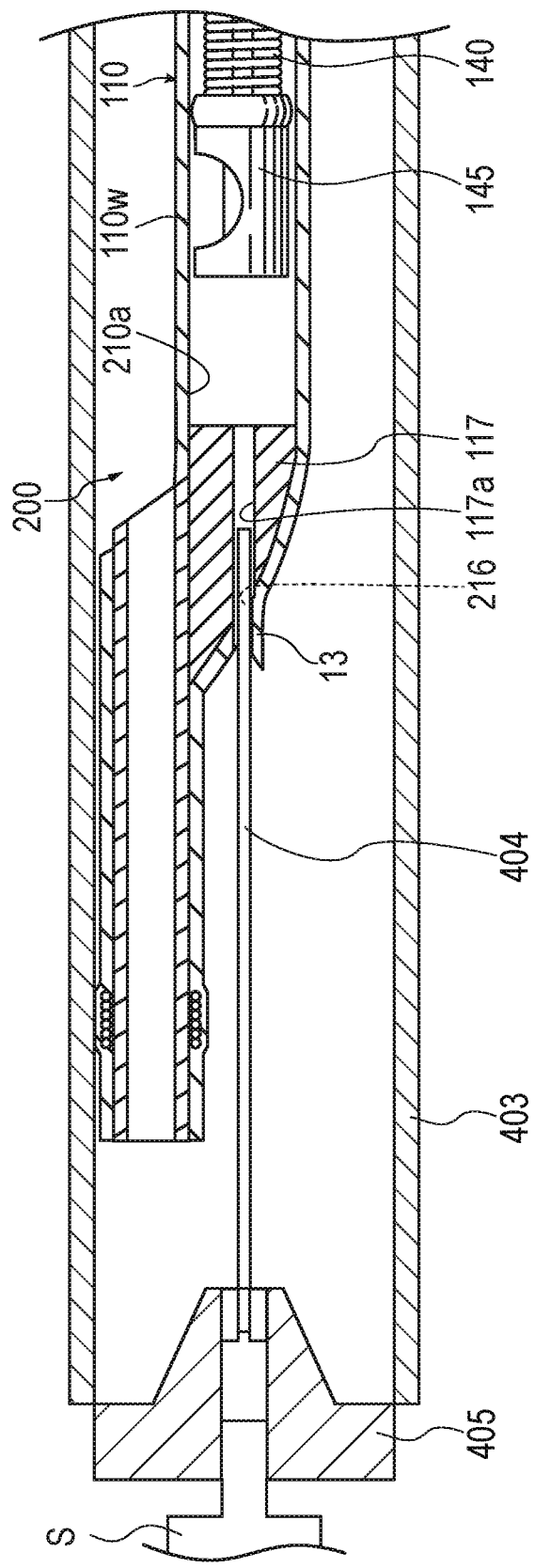
FIG. 8 is a view illustrating a mode in which the diagnostic imaging catheter of the second embodiment is primed.
Figure 9A:
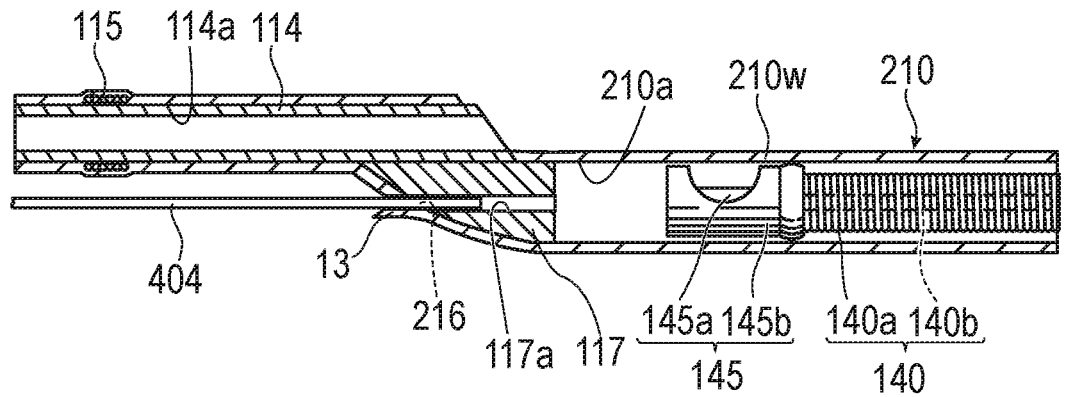
Figure 9B:
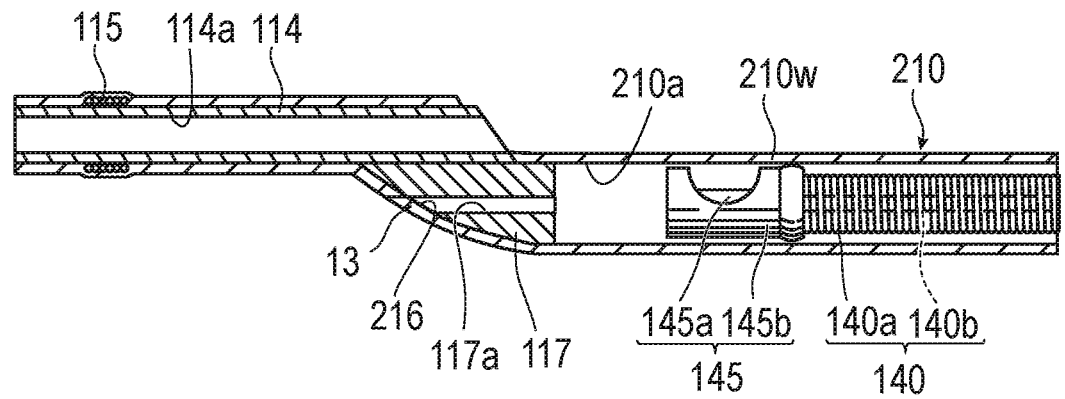

FIG. 7 is a side view illustrating a state in which a diagnostic imaging catheter 200 of a second embodiment is accommodated inside a holder tube 400. FIG. 8 is a view illustrating a mode in which the diagnostic imaging catheter 200 of the second embodiment is primed. FIGS. 9A and 9B show views illustrating the configuration of a distal side of the diagnostic imaging catheter 200 of the second embodiment.

Hereinafter, a valve body 13 of the diagnostic imaging catheter 200 of the second embodiment will be described with reference to FIGS. 7 to 9B. The same reference signs are assigned to the same configuration elements as those in the first embodiment, and description thereof is omitted.

In the diagnostic imaging catheter 100 of the first embodiment, the valve body 10 is formed on the side surface of the sheath 110. As illustrated in FIGS. 9A and 9B, the diagnostic imaging catheter 200 of the second embodiment is different from that of the first embodiment in that the valve body 13 is formed on a distal surface of a sheath 210.

During a period of time prior to using the diagnostic imaging catheter 200 used (for example, a period of time from the shipment of manufactured products to the connection of a product to the external apparatus 300 for use), as illustrated in FIG. 7, the sheath 210 of the diagnostic imaging catheter 200 is accommodated in the holder tube 400.

The holder tube 400 helps prevent the occurrence of damage to the sheath 210, which is caused by the rubbing of the sheath 210 against peripherals, by accommodating the sheath 210 of the diagnostic imaging catheter 200 during transportation. The holder tube 400 is configured of a hollow long member having such flexibility that the holder tube 400 can be manually wound. Resins such as polyethylene and polypropylene may be used as the material of the holder tube 400.

As illustrated in FIG. 7, an opening portion 401 is formed at one end of the holder tube 400, and an opening portion 402 is formed at the other end of the holder tube 400. In accordance with an exemplary embodiment, the sheath 210 can be accommodated in the holder tube 400 by inserting a distal side of the sheath 210 into the holder tube 400 via the opening portion 401 at the one end of the holder tube 400, and pushing the sheath 210.

A connector port 403 is installed in the opening portion 402 formed at the other end of the holder tube 400, and a syringe or the like can be connected to the connector port 403 so as to supply priming liquid. The connector port 403 is connected to the syringe S when priming the holder tube 400.

As illustrated in FIG. 8, a hub 405 including a priming needle (equivalent to an "insertion member") 404 is attached to an end portion of the connector port 403. The priming needle 404 is inserted into a lumen 210a of the sheath 210 via a communicating hole 216. As illustrated in FIG. 9A, the priming needle 404 maintains the valve body 13 in an "open state" in which the communicating hole 216 is open.

A priming process is performed via the communicating hole 216. As illustrated in FIG. 8, a user connects the syringe S, which is filled with priming liquid, to the connector port 403, and injects the priming liquid into the priming needle 404 via the hub 405 by pressing the plunger of the syringe S. The priming liquid is injected into a distal end of the sheath 210 via the priming needle 404. Accordingly, liquid pressure in the vicinity of the ultrasound transducer 145a installed in a distal portion increases, and air bubbles are unlikely to stick to a surface of the ultrasound transducer 145a. The priming process is performed by accommodating the diagnostic imaging catheter 200 in the holder tube 400, and injecting a medium such as a physiological salt solution into the sheath 210 up to a proximal portion.

The user takes the diagnostic imaging catheter 200 out from the holder tube 400 when starting using the diagnostic imaging catheter 200. At this time, the priming needle 404 maintaining the valve body 13 in an open state is removed from the communicating hole 216. As a result, as illustrated in FIG. 9B, the valve body 13 enters in a "closed state" in which the communicating hole 216 is covered and blocked with the valve body 13. As illustrated in FIG. 2A, the port 162 is open to the atmosphere while communicating with the inside of the lumen 210a of the sheath 210. For this reason, the inside of the lumen 210a is in a state of equilibrium with the atmospheric pressure. Since the external pressure and the internal pressure of the sheath 210 are in a state of equilibrium, the valve body 13 is maintained in a closed state.

Similar to the first embodiment, the valve body 13 may include a restriction unit that restricts the valve body 13 from entering the inside of the sheath 210.

As described above, in the diagnostic imaging catheter 200 of the second embodiment, the communicating hole 216 is formed on the distal surface of the sheath 210. The valve body 13 is configured to be capable of switching between an open state and a closed state with the aid of the priming needle 404 that is inserted into the lumen of the sheath 210 via the communicating hole 216.

In the diagnostic imaging catheter 200 having such a configuration, if the priming needle 404 is inserted into the communicating hole 216, the valve body 13 enters an open state in which the communicating hole 216 is open. As a result, the priming liquid can be injected into the sheath 210. In contrast, if the priming needle 404 is drawn from the communicating hole 216, the valve body 13 enters a closed state in which the communicating hole 216 is covered and blocked with the valve body 13. As a result, the infiltration of air or blood into the sheath 210 from the outside of the sheath 210 can be prevented.

The diagnostic imaging catheter of the present invention has been described with reference to the embodiments and the modification examples; however, the present invention is not limited to only the configurations described in the embodiments and the modification examples, and the embodiments and the modification examples can be suitably changed based on the claims.

In the first embodiment, the valve body is configured such that the valve body can be maintained in a closed state by pressing force received from the guide wire inserted into the guide wire lumen; however, the present invention is not limited to that configuration. The valve body may be configured to include a check valve structure such that the flowing of priming liquid from the inside of the sheath to the outside is allowed, and a flow from the outside of the sheath to the inside of the sheath is limited. Alternatively, as in the second embodiment, the valve body may be configured such that the valve body can be maintained in a closed state by a relationship between the external pressure and the internal pressure of the sheath.

In the second embodiment, an insertion member is the priming needle; however, insofar as a member can be inserted into the communicating hole, and is capable of maintaining the valve body in an open state, the member is not limited to a priming needle.

An intravascular ultrasound (IVUS) is exemplified as a target to which the diagnostic imaging catheter of the present invention is applied; however, insofar as an application target is an imaging apparatus for diagnosis which an operator can use by disposing a sensor at a desired position while confirming the position of the sensor on an X-ray image, the present invention is not limited to a specific imaging apparatus for diagnosis. For example, the present disclosure can be applied to a dual type imaging apparatus for diagnosis that has both functions of an intravascular ultrasound and an optical coherence tomography (OCT), and is capable of switching between both functions, or both functions can be used simultaneously.

The detailed description above describes a diagnostic imaging catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A diagnostic imaging catheter comprising:
   a drive shaft, of which a distal portion is provided with a signal transmitting and receiving unit, and wherein the drive shaft is configured to be rotated;
   a sheath including a lumen into which the drive shaft is inserted such that the drive shaft is configured to be moved forward and backward;
   a communicating hole formed at a tubular wall of the sheath in a distal portion of the sheath, through which an inside and an outside of the lumen communicate with each other;
   a valve body capable of opening and closing the communicating hole, wherein the valve body is configured to be capable of switching between a closed state in which the communicating hole is covered and blocked with the valve body and an open state which the valve body enters by being moved to the outside of the sheath from the closed state, and in which the communicating hole is open;
   a guide wire insertion member attached to a side surface of a distal portion of the sheath, the guide wire insertion member having a guide wire lumen disposed outside the lumen of the sheath, extending in an axial direction of the sheath from a proximal end opening to a distal end opening and configured to receive a guide wire through the proximal end opening and the distal end opening, wherein the guide wire lumen of the guide wire insertion member is parallel to the lumen of the sheath, the communicating hole is configured to communicate with the lumen and the guide wire lumen, and the lumen of the sheath and the guide wire lumen of the guide wire insertion member communicate with each other through the communicating hole formed at a position between the proximal end opening and the distal end opening in the axial direction of the sheath; and
   wherein the valve body includes a flap defined by a slit passing through the tubular wall of the sheath up to the inside of the lumen of the sheath and forming an outer edge of the communicating hole, and wherein a distal end of the flap is continuous to the tubular wall of the sheath and a proximal end of the flap is deformable in a radial direction of the sheath in relation to the distal end of the flap between the closed state in which the proximal end of the flap covers the communicating hole and the open state in which the proximal end of the flap is deformed away from the communicating hole.

2. The diagnostic imaging catheter according to claim 1, further comprising:
   a restriction unit configured to restrict the valve body from entering the inside of the sheath by being attached to the tubular wall of the sheath when the valve body is in the closed state.

3. The diagnostic imaging catheter according to claim 2, wherein the restriction unit includes a cutout portion formed by cutting out a portion of the tubular wall of the sheath, and
   wherein the valve body in the closed state is attached to the cutout portion.

4. The diagnostic imaging catheter according to claim 3, wherein the restriction unit includes an attachment portion that is formed integrally with the valve body and is attached to an exterior surface of the tubular wall when the valve body is in the closed state.

5. The diagnostic imaging catheter according to claim 2, wherein the restriction unit includes an attachment portion that is formed integrally with the valve body and is attached to an exterior surface of the tubular wall when the valve body is in the closed state.

6. The diagnostic imaging catheter according claim 1, wherein the valve body is configured such that the valve body can be maintained in the closed state by pressing force received from the guide wire inserted into the guide wire lumen.

7. The diagnostic imaging catheter according to claim 1, wherein the valve body has a U-shape.

8. The diagnostic imaging catheter according to claim 1, wherein the guide wire insertion member has a marker having X-ray contrast properties.

9. A diagnostic imaging catheter comprising:
   a rotatable drive shaft, of which a distal portion is provided with a signal transmitting and receiving unit;
   a sheath including a lumen into which the drive shaft is inserted such that the drive shaft is configured to be moved forward and backward;
   a communicating hole formed at a tubular wall of the sheath in a distal portion of the sheath, and through which an inside and an outside of the lumen communicate with each other;
   a valve body capable of opening and closing the communicating hole, wherein the valve body is configured to be capable of switching between a closed state in which the communicating hole is covered and blocked with the valve body and an open state which the valve body enters by being moved to the outside of the sheath from the closed state, and in which the communicating hole is open;
   a guide wire insertion member attached to a side surface of a distal portion of the sheath and including a guide wire lumen disposed outside of the lumen of the sheath and extending in an axial direction of the sheath from a proximal end opening to a distal end opening parallel to the lumen of the sheath, into which a guide wire can be inserted through the proximal end opening and the distal end opening, wherein the communicating hole is configured to communicate with the lumen and the guide wire lumen, the lumen of the sheath and the guide wire lumen of the guide wire insertion member communicate with each other through the communicating hole formed at a position between the proximal end opening and the distal end opening in the axial direction of the sheath, and the valve body is configured such that the valve body can be maintained in the closed state by pressing force received from the guide wire inserted into the guide wire lumen;

a restriction unit configured to restrict the valve body from entering the inside of the sheath by being attached to the tubular wall of the sheath when the valve body is in the closed state; and wherein the valve body includes a flap defined by a slit passing through the tubular wall of the sheath up to the inside of the lumen of the sheath and forming an outer edge of the communicating hole, and wherein a distal end of the flap is continuous to the tubular wall of the sheath and a proximal end of the flap is deformable in a radial direction of the sheath in relation to the distal end of the flap between the closed state in which the proximal end of the flap covers the communicating hole and the open state in which the proximal end of the flap is deformed away from the communicating hole.

10. The diagnostic imaging catheter according to claim 9,
wherein the restriction unit includes a cutout portion formed by cutting out a portion of the tubular wall of the sheath, and
wherein the valve body in the closed state is attached to the cutout portion.

11. The diagnostic imaging catheter according to claim 10,
wherein the restriction unit includes an attachment portion that is formed integrally with the valve body and is attached to an exterior surface of the tubular wall when the valve body is in the closed state.

12. The diagnostic imaging catheter according to claim 9,
wherein the restriction unit includes an attachment portion that is formed integrally with the valve body and is attached to an exterior surface of the tubular wall when the valve body is in the closed state.

* * * * *